(12) United States Patent
Song et al.

(10) Patent No.: US 11,911,159 B2
(45) Date of Patent: Feb. 27, 2024

(54) METHOD, SYSTEM AND NON-TRANSITORY COMPUTER-READABLE RECORDING MEDIUM FOR CALCULATING INFORMATION RELATING TO URINATION

(71) Applicant: Dain Technology, Inc., Seoul (KR)

(72) Inventors: Jee Young Song, Seoul (KR); Ji Young Jung, Yongin-si (KR); On Sub Kim, Anyang-si (KR)

(73) Assignee: Dain Technology, Inc., Seoul (KR)

( * ) Notice: Subject to any disclaimer, the term of this patent is extended or adjusted under 35 U.S.C. 154(b) by 709 days.

(21) Appl. No.: 16/662,256

(22) Filed: Oct. 24, 2019

(65) Prior Publication Data

US 2020/0054265 A1 Feb. 20, 2020

Related U.S. Application Data

(63) Continuation of application No. PCT/KR2018/012443, filed on Oct. 19, 2018.

(30) Foreign Application Priority Data

Jun. 29, 2018 (KR) .................. 10-2018-0075203

(51) Int. Cl.
*A61B 5/20* (2006.01)
*A61B 5/11* (2006.01)
*G10L 25/66* (2013.01)

(52) U.S. Cl.
CPC .............. *A61B 5/208* (2013.01); *A61B 5/11* (2013.01); *G10L 25/66* (2013.01)

(58) Field of Classification Search
None
See application file for complete search history.

(56) References Cited

U.S. PATENT DOCUMENTS

| | | | | |
|---|---|---|---|---|
| 8,276,465 B2† | 10/2012 | Belotserkovsky | | |
| 9,084,571 B2† | 7/2015 | Belotserkovsky | | |
| 11,207,012 B2* | 12/2021 | Belotserkovsky | ..... | A61B 5/202 |
| 2008/0082022 A1* | 4/2008 | Brohan | ................ | A61B 5/208 |
| | | | | 600/573 |
| 2008/0262389 A1* | 10/2008 | Shahar | ..................... | A61B 7/04 |
| | | | | 600/586 |
| 2008/0275366 A1* | 11/2008 | Brohan | ................ | A61B 5/208 |
| | | | | 600/584 |
| 2008/0312538 A1* | 12/2008 | Shahar | .................. | A61B 7/026 |
| | | | | 600/459 |
| 2011/0125061 A1* | 5/2011 | Shahar | .................. | A61B 5/208 |
| | | | | 600/586 |
| 2012/0048033 A1* | 3/2012 | Belotserkovsky | ...... | G01F 1/666 |
| | | | | 73/861.18 |

(Continued)

*Primary Examiner* — Benjamin S Melhus
(74) *Attorney, Agent, or Firm* — Dinsmore & Shohl LLP; Yongsok Choi, Esq.

(57) ABSTRACT

According to one aspect of the invention, there is provided a method for calculating information on urination. The method includes the steps of acquiring a sound signal related to urination of a user, calculating a urination parameter related to an effective value (or urination parameters related to an effective value and a spectral centroid) from the acquired sound signal, and estimating a urine flow rate of the user with reference to the calculated urination parameter.

6 Claims, 3 Drawing Sheets

(56) References Cited

U.S. PATENT DOCUMENTS

| | | | |
|---|---|---|---|
| 2012/0053540 A1* | 3/2012 | Belotserkovsky | A61B 5/208 604/317 |
| 2014/0018702 A1* | 1/2014 | Belotserkovsky | A61B 5/208 600/584 |
| 2016/0029942 A1* | 2/2016 | Paulsen | G16H 15/00 702/19 |
| 2016/0113562 A1† | 4/2016 | Belotserkovsky | |
| 2016/0183803 A1* | 6/2016 | Mosli | A61B 10/007 600/573 |
| 2017/0086728 A1* | 3/2017 | Hidas | A61B 5/0022 |
| 2019/0008439 A1* | 1/2019 | Sageder | G01N 33/493 |
| 2020/0178906 A1* | 6/2020 | Bevan | A61B 5/02055 |

\* cited by examiner
† cited by third party

METHOD, SYSTEM AND NON-TRANSITORY COMPUTER-READABLE RECORDING MEDIUM FOR CALCULATING INFORMATION RELATING TO URINATION

CROSS-REFERENCE TO RELATED APPLICATIONS

This application is a continuation application of Patent Cooperation Treaty (PCT) international application Serial No. PCT/KR2018/012443, filed on Oct. 19, 2018, which claims priority to Korean Patent Application Serial No. 10-2018-0075203, filed on Jun. 29, 2018. The entire contents of PCT international application Serial No. PCT/KR2018/012443 and Korean Patent Application Serial No. 10-2018-0075203 are hereby incorporated by reference.

FIELD OF THE INVENTION

The present invention relates to a method, system, and non-transitory computer-readable recording medium for calculating information on urination.

BACKGROUND

Uroflow, which means the rate of urine flow, is influenced by organs associated with urination (e.g., urethra, bladder, prostate, etc.), various diseases, psychological factors, or other external factors, and serves as important basic data for assessing a urination status of a patient.

In this regard, urologists recommend uroflowmetry to patients who complain of diseases or symptoms related to urination. In general, the uroflowmetry is carried out by measuring the amount of urine of a user per unit time through a balance for measuring weight of a container and a computer connected to the balance when the user discharges urine in the container. In particular, since the uroflowmetry is a non-invasive and simple technique, it is widely used for diagnosis and prognostic management of various diseases, such as prostate hyperplasia, cystitis and irritable bladder syndrome, and observation of functional recovery after surgery on pelvic organs.

However, the uroflowmetry carried out by the techniques introduced so far, as well as the above-described conventional technique, has the following two problems.

First, since the uroflowmetry should be carried out when a user visits a hospital, the user experiences tension or discomfort due to being in a situation and setting that the user does not experience in day-to-day life, making it difficult to accurately carry out the uroflowmetry.

Secondly, although the uroflowmetry should be carried out a sufficient number of times over a wide period of time in order to obtain accurate information that can be referred to in a diagnosis of a patient, it is difficult to obtain the accurate information since the uroflowmetry can be carried out only when the patient visits a hospital. Further, when the patient cannot visit the hospital, the diagnosis can only be based on the patient's subjective sensation.

In this connection, the present disclosure presents a technique for easily and accurately estimating information on urination anytime or anywhere, using a urination parameter related to an effective (or root mean square (RMS)) value (or urination parameters related to an effective (RMS) value and a spectral centroid) calculated from a sound signal related to urination of a user.

SUMMARY OF THE INVENTION

One object of the present invention is to solve all the above-described problems in the prior art.

Another object of the invention is to accurately and easily estimate a urine flow rate, urination start and end points, a voided urine volume, and the like from a sound signal related to urination of a user.

Yet another object of the invention is to accurately estimate information on urination of a user regardless of the type and material of a container (or toilet bowl) in which urine of the user is contained.

Still another object of the invention is to specify the sex of a user who urinates.

Still yet another object of the invention is to accurately estimate information on urination of a user using a urination information estimation model according to the sex of the user.

Further another object of the invention is to allow a user to personally estimate information on urination of the user without visiting a hospital.

The representative configurations of the invention to achieve the above objects are described below.

According to one aspect of the invention, there is provided a method for calculating information on urination, comprising the steps of: acquiring a sound signal related to urination of a user; calculating a urination parameter related to an effective value (or urination parameters related to an effective value and a spectral centroid) from the acquired sound signal; and estimating a urine flow rate of the user with reference to the calculated urination parameter.

According to another aspect of the invention, there is provided a system for calculating information on urination, comprising: a sound signal acquisition unit configured to acquire a sound signal related to urination of a user; a urination parameter calculation unit configured to calculate a urination parameter related to an effective value (or urination parameters related to an effective value and a spectral centroid) from the acquired sound signal; and a urination information estimation unit configured to estimate a urine flow rate of the user with reference to the calculated urination parameter.

In addition, there are further provided other methods and systems to implement the invention, as well as non-transitory computer-readable recording media having stored thereon computer programs for executing the methods.

According to the invention, it is possible to accurately and easily estimate a urine flow rate, urination start and end points, a voided urine volume, and the like from a sound signal related to urination of a user.

According to the invention, it is possible to accurately estimate information on urination of a user regardless of the material of a container (or toilet bowl) in which urine of the user is contained.

According to the invention, it is possible to specify the sex of a user who urinates.

According to the invention, it is possible to accurately estimate information on urination of a user using a urination information estimation model according to the sex of the user.

According to the invention, it is possible to allow a user to personally estimate information on urination of the user without visiting a hospital.

DETAILED DESCRIPTION

Figure 1:
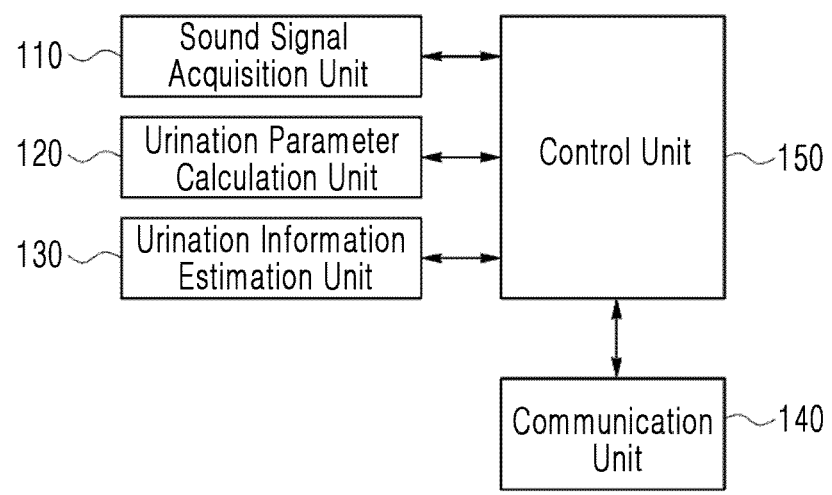
FIG. 1 specifically shows the internal configuration of a urination information estimation system according to one embodiment of the invention.

In the following detailed description of the present invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures, and characteristics described herein may be implemented as modifications from one embodiment to another without departing from the spirit and scope of the invention. Furthermore, it shall be understood that the positions or arrangements of individual elements within each embodiment may also be modified without departing from the spirit and scope of the invention. Therefore, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, various preferred embodiments of the present invention will be described in detail with reference to the accompanying drawings to enable those skilled in the art to easily implement the invention.

Configuration of a Urination Information Estimation System

Hereinafter, the internal configuration of a urination information estimation system crucial for implementing the invention and the functions of the respective components thereof will be discussed.

FIG. 1 specifically shows the internal configuration of a urination information estimation system 100 according to one embodiment of the invention.

Referring to FIG. 1, the urination information estimation system 100 according to one embodiment of the invention may comprise a sound signal acquisition unit 110, a urination parameter calculation unit 120, a urination information estimation unit 130, a communication unit 140, and a control unit 150. According to one embodiment of the invention, at least one of the sound signal acquisition unit 110, the urination parameter calculation unit 120, the urination information estimation unit 130, the communication unit 140, and the control unit 150 may be program modules that communicate with an external system (not shown). The program modules may be included in the urination information estimation system 100 in the form of operating systems, application program modules, and other program modules, and may be physically stored in a variety of commonly known storage devices. Further, the program modules may also be stored in a remote storage device that may communicate with the urination information estimation system 100. Meanwhile, such program modules may include, but are not limited to, routines, subroutines, programs, objects, components, and data structures for performing specific tasks or executing specific abstract data types according to the invention, as will be described below.

Meanwhile, although the urination information estimation system 100 has been described above, the above description is illustrative, and it will be apparent to those skilled in the art that at least a part of the functions or components of the urination information estimation system 100 may be implemented or included in a device 200 to be described, as necessary. Further, in some cases, all the functions and components of the urination information estimation system 100 may be implemented or included in the device 200.

The device 200, according to one embodiment of the invention, is digital equipment having a memory means and a microprocessor for computing capabilities, and may include a wearable device, such as smart glasses, a smart watch, a smart band, a smart ring, a smart necklace, a smart earset, smart earphones, and smart earrings, or include a somewhat traditional device such as a smart phone, a smart pad, a desktop computer, a notebook computer, a workstation, a personal digital assistant (PDA), a web pad, a mobile phone, and a remote controller. Besides the foregoing examples, the device 200 may be changed without limitation as long as the objects of the invention may be achieved. Further, the device 200, according to one embodiment of the invention, may include a sound acquisition (or sound detection) module (e.g., a microphone) for acquiring a sound signal (e.g., a sound signal related to urination or surroundings), and may include a motion detection module, an acceleration sensor module, or a gyroscope sensor module for detecting a motion of a user.

Meanwhile, the device 200, according to one embodiment of the invention, may include an application that assists in estimating information on urination according to the invention. The application may be downloaded from an external application distribution server (not shown). The characteristics of the program module may be generally similar to those of the sound signal acquisition unit 110, the urination parameter calculation unit 120, the urination information estimation unit 130, the communication unit 140, and the control unit 150 of the urination information estimation system 100 to be described below. Here, at least a part of the application may be replaced with a hardware device or a firmware device that may perform a substantially equal or equivalent function, as necessary.

First, the sound signal acquisition unit 110, according to one embodiment of the invention, may acquire a sound signal related to urination of a user.

For example, according to one embodiment of the invention, a sound signal may be generated as urine hits a toilet bowl or comes in contact with water in the toilet bowl while the user urinates, and the sound signal acquisition unit 110 may acquire the generated sound signal as a sound signal related to the urination of the user.

As another example, according to one embodiment of the invention, various noises may be generated from the user or surroundings of the user while the user urinates, and the sound signal acquisition unit 110 may acquire a sound signal including a sound signal generated by the urination or the user (e.g., a sound signal generated as urine comes in contact with water in a toilet bowl) and a sound signal related to the above noises as a sound signals related to the urination of the user.

Meanwhile, according to one embodiment of the invention, a predetermined trigger indicating that urination starts or ends (e.g., a voice trigger or a trigger caused by a button of the device 200) may be provided by the user, and a sound signal acquired between a urination start point and a urination end point according to the trigger may be specified as a sound signal related to the urination of the user.

Next, the urination parameter calculation unit 120, according to one embodiment of the invention, may calculate a urination parameter related to an effective (or a root mean square (RMS)) value from the sound signal acquired by the sound signal acquisition unit 110.

Specifically, the urination parameter calculation unit 120, according to one embodiment of the invention, may analyze the sound signal acquired by the sound signal acquisition unit 110 in a time domain to calculate a urination parameter related to an effective (RMS) value of the sound signal.

Further, the urination parameter calculation unit 120, according to one embodiment of the invention, may calculate a urination parameter related to a spectral centroid from the sound signal acquired by the sound signal acquisition unit 110.

Specifically, the urination parameter calculation unit 120, according to one embodiment of the invention, may analyze the sound signal acquired by the sound signal acquisition unit 110 in a frequency domain to calculate a urination parameter related to a spectral centroid of the sound signal.

Meanwhile, the urination parameter calculation unit 120, according to one embodiment of the invention, may divide the acquired sound signal into a plurality of sections on the basis of a predetermined time or frequency and calculate a urination parameter related to an effective (RMS) value or a spectral centroid for each of the sections.

Next, the urination information estimation unit 130, according to one embodiment of the invention, may estimate a urine flow rate (e.g., a urine flow rate over time or a voided urine volume over time) of the user with reference to the urination parameter calculated by the urination parameter calculation unit 120.

For example, when a urination parameter related to an effective (RMS) value is calculated for each of a plurality of sections (i.e., a plurality of frequency bands) of the acquired sound signal divided on the basis of a predetermined frequency (specifically, calculated by the urination parameter calculation unit 120), the urination information estimation unit 130 according to one embodiment of the invention may estimate a urine flow rate of the user on the basis of at least one urine flow rate prediction model in which the urination parameter related to the effective value for each of the sections is used as a variable.

As another example, when urination parameters related to an effective value and a spectral centroid are calculated for each of a plurality of sections of the acquired sound signal divided on the basis of a predetermined time, the urination information estimation unit 130, according to one embodiment of the invention, may estimate a urine flow rate of the user on the basis of at least one urine flow rate prediction model in which the urination parameters related to the effective value and the spectral centroid for each of the sections are used as variables.

Further, the urination information estimation unit 130, according to one embodiment of the invention, may determine sex of the user on the basis of a frequency of a sound generated at the start of the urination or during the urination, and specify a urine flow rate prediction model for estimating a urine flow rate on the basis of the determined sex of the user.

For example, according to one embodiment of the invention, due to the structures (specifically, urethra, urinary organs, etc.) of a male or female body, a sound corresponding to a predetermined frequency (or a predetermined frequency band) may be generated at the start of the urination or during the urination (particularly, such a sound may be louder in the case of females), and sex of the user may be determined on the basis of whether the acquired sound signal (specifically, a sound signal of a section corresponding to the urination duration in the acquired sound signal) contains the sound corresponding to the predetermined frequency (or the predetermined frequency band). Further, according to one embodiment of the invention, the urination information estimation unit 130 may estimate a urine flow rate of the user using a urine flow rate prediction model corresponding to the determined sex of the user.

Further, the urination information estimation unit 130, according to one embodiment of the invention, may further estimate a start point and an end point of the urination of the user with reference to the calculated urination parameter.

For example, the urination information estimation unit 130, according to one embodiment of the invention, may statistically analyze a primary urination parameter related to the effective value or spectral centroid to calculate a secondary urination parameter (e.g., a variance, a standard deviation, or a rate of sound level change) related to the urination of the user, and estimate a start point and an end point of the urination of the user on the basis of the calculated secondary urination parameter.

More specifically, the urination information estimation unit 130, according to one embodiment of the invention, may statistically analyze a sound signal associated with a certain spectral centroid (i.e., a primary urination parameter) in the sound signal related to the urination of the user to calculate a rate of sound level change (i.e., a secondary urination parameter) corresponding to the sound signal and estimate a start point or an end point of the urination on the basis of a time point when the rate of sound level change is sharply increased.

Further, the urination information estimation unit 130, according to one embodiment of the invention, may estimate a voided urine volume of the user on the basis of the estimated start and end points of the urination and the estimated urine flow rate.

For example, the urination information estimation unit 130, according to one embodiment of the invention, may perform an operation on (e.g., take an integral of) the estimated urine flow rate in a section between the estimated start and end points of the urination to estimate a voided urine volume of the user. The urination information estimation unit 130, according to one embodiment of the invention, may also estimate an average urine flow rate on the basis of the estimated urination duration (i.e., the difference between the start and end points of the urination) and the estimated voided urine volume.

Further, the urination information estimation unit 130, according to one embodiment of the invention, may perform filtering for removing noises from the sound signal acquired by the sound signal acquisition unit 110.

For example, with reference to information on frequency patterns related to various noises, such as a human speech sound (i.e., a voice), a water sound, and a sound of a door closing (e.g., a toilet door closing), the urination information estimation unit 130, according to one embodiment of the invention, may filter noises by removing sound signals having the frequency patterns related to the various noises from the sound signal related to the urination of the user.

As another example, the urination information estimation unit 130, according to one embodiment of the invention, may filter noises by removing sound signals in frequency bands other than those associated with urination (information on the frequency bands associated with urination may be predetermined by analyzing information on urination of multiple users) from the sound signal related to the urination of the user.

As yet another example, the urination information estimation unit 130, according to one embodiment of the invention, may filter noises by removing sound signals associated with noises (e.g., noises in the form of impulses) from the sound signal related to the urination of the user.

Further, the urination information estimation unit 130, according to one embodiment of the invention, may filter noises on the basis of a spectral centroid calculated from the sound signal related to the urination of the user.

For example, the urination information estimation unit 130, according to one embodiment of the invention, may track changes in a spectral centroid of the sound signal related to the urination of the user on the basis of the calculated spectral centroid, and filter noises by removing sound signals in frequency bands that deviate from the spectral centroid beyond a predetermined level.

Meanwhile, the urination information estimation unit 130, according to one embodiment of the invention, may specify a start point and an end point for noise filtering with reference to the estimated start and end points of the urination of the user, and perform preprocessing for noise filtering by removing sections other than the specified start and end points.

Figure 2:
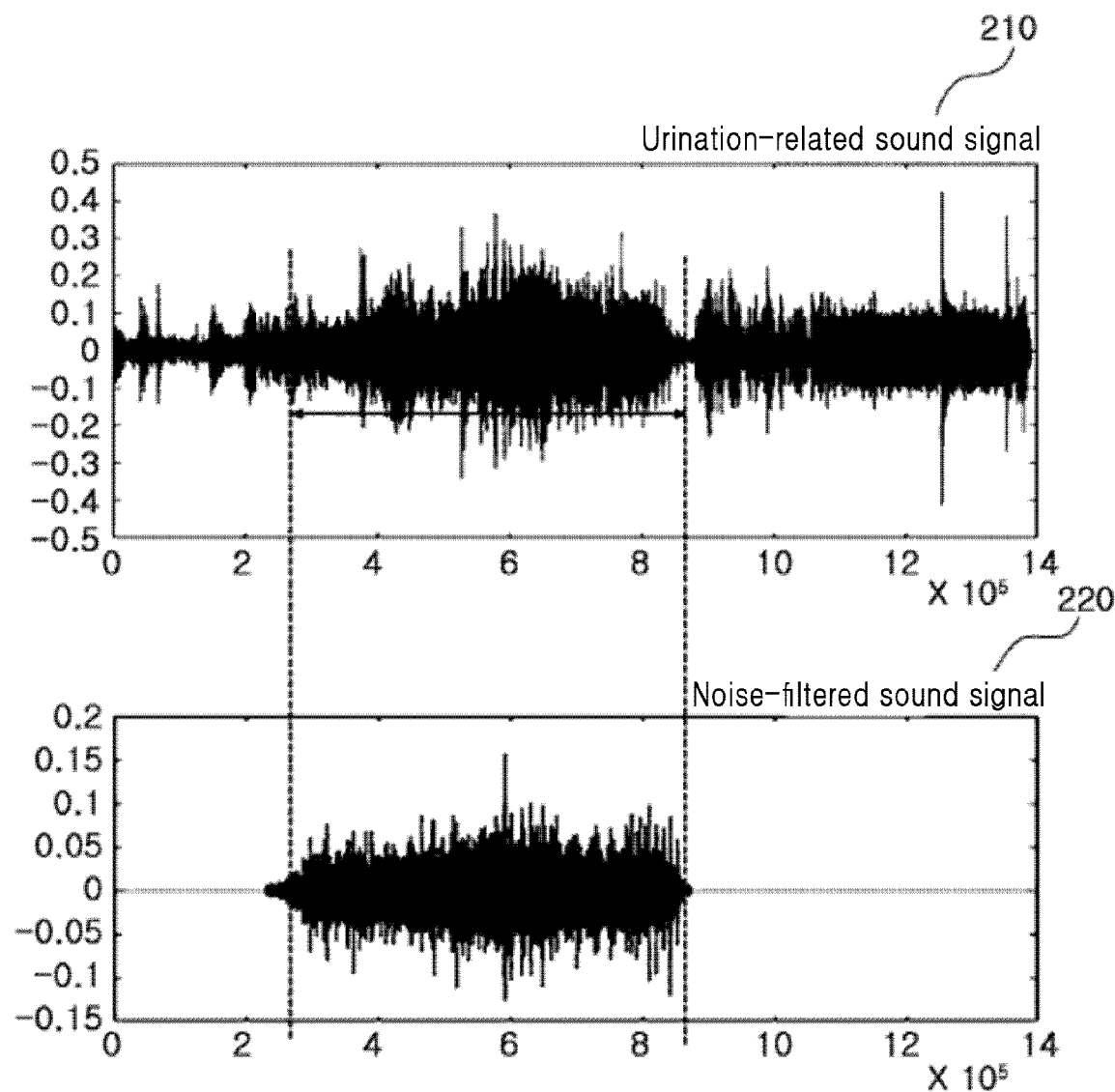
FIG. 2 illustratively shows a sound signal according to one embodiment of the invention and another sound signal obtained by removing noises from the sound signal.

For example, FIG. 2 illustratively shows sound signals 210 and 220 before and after the urination information estimation unit 130, according to one embodiment of the invention, performs the above preprocessing and noise filtering. Here, according to one embodiment of the invention, the horizontal axis may represent time (specifically, in the unit of $\frac{1}{44100}$ seconds) and the vertical axis may represent sound pressure.

Further, the urination information estimation unit 130, according to one embodiment of the invention, may estimate a urine flow rate of the user with further reference to information on a place where the sound signal is acquired.

For example, the urination information estimation unit 130, according to one embodiment of the invention, may analyze the sound signal related to the urination of the user (e.g., analyze reverberation caused by the sound signal) to specify an area or structure of a place where the sound signal is acquired and estimate a urine flow rate of the user using a urine flow rate prediction model corresponding to the area or structure.

Further, the urination information estimation unit 130, according to one embodiment of the invention, may generate a voiding diary of the user on the basis of at least one of the estimated urine flow rate, urination duration (i.e., the difference between the start and end points of the urination), and voided urine volume. According to one embodiment of the invention, the voiding diary may include information on not only a urine flow rate, a urination duration (i.e., a difference between start and end points of urination), and a voided urine volume by day or hour, but also an average urine flow rate, an average urination duration, an average voided urine volume, a maximum urine flow rate, a maximum urination duration, and a maximum voided urine volume calculated by statistically analyzing at least one of the urine flow rate, urination duration, and voided urine volume.

Further, the urination information estimation unit 130 according to one embodiment of the invention may generate an analysis comment on the urination of the user with reference to the generated voiding diary.

For example, the urination information estimation unit 130, according to one embodiment of the invention, may compare and analyze a urination pattern appearing in the voiding diary of the user and a predetermined reference urination pattern to specify abnormal urination of the user, and generate an analysis comment from information on a time when the abnormal urination occurs, a urine flow rate of the abnormal urination, a voided urine volume of the abnormal urination, and a reason for specifying the abnormal urination. Meanwhile, according to one embodiment of the invention, at least a part of the analysis comment on the urination may be similar to the contents of a conventional chart used for a medical insurance claim.

Next, the communication unit 140, according to one embodiment of the invention, may function to enable data transmission/reception from/to the sound signal acquisition unit 110, the urination parameter calculation unit 120, and the urination information estimation unit 130.

Lastly, the control unit 150, according to one embodiment of the invention, may function to control data flow among the sound signal acquisition unit 110, the urination parameter calculation unit 120, the urination information estimation unit 130, and the communication unit 140. That is, the control unit 150 may control data flow into/out of the urination information estimation system 100 or data flow among the respective components of the urination information estimation system 100, such that the sound signal acquisition unit 110, the urination parameter calculation unit 120, the urination information estimation unit 130, and the communication unit 140 may carry out their particular functions, respectively.

Figure 3:
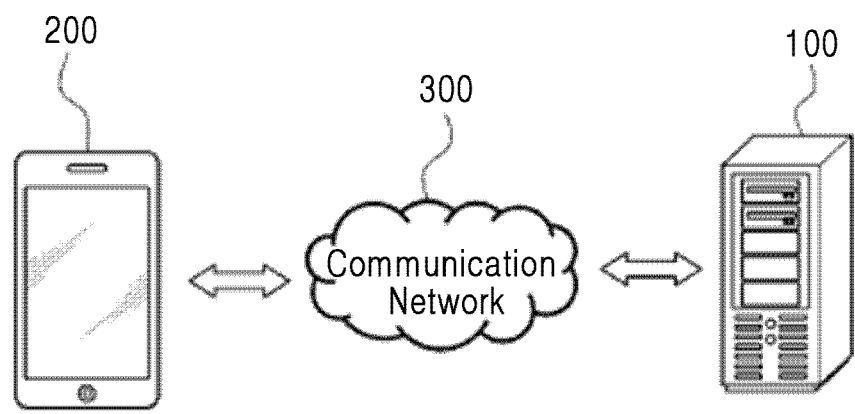
FIG. 3 illustratively shows how to estimate information on urination of a user according to one embodiment of the invention.

FIG. 3 illustratively shows how to estimate information on urination of a user according to one embodiment of the invention.

Referring to FIG. 3, it may be assumed that a server system including the urination information estimation system 100 according to the invention is interconnected with a device 200 of a user via a communication network 300.

In this case, the communication network 300, according to one embodiment of the invention, may be implemented regardless of communication modality, such as wired and wireless communications, and may be constructed from a variety of communication networks, such as local area networks (LANs), metropolitan area networks (MANs), and wide area networks (WANs). Preferably, the communication network 300 described herein may be the Internet or the World Wide Web (WWW). However, the communication network 300 is not necessarily limited thereto, and may at least partially include known wired/wireless data communication networks, known telephone networks, or known wired/wireless television communication networks.

For example, the communication network 300 may be a wireless data communication network, at least a part of which may be implemented with a conventional communication scheme, such as WiFi communication, WiFi-Direct communication, Long Term Evolution (LTE) communication, Bluetooth communication (more specifically, Bluetooth Low Energy (BLE) communication), infrared communication, and ultrasonic communication.

First, according to one embodiment of the invention, a sound signal related to urination of the user may be acquired by the device 200 of the user, and the acquired sound signal may be provided to the urination information estimation system 100 via the communication network 300.

Meanwhile, according to one embodiment of the invention, a deviation of the acquired sound signal may occur according to positions, a number, types, kinds, characteristics, and the like of sound acquisition modules (e.g., microphones) of the device 200, and the urination information estimation system 100, according to one embodiment of the invention, may correct the deviation.

For example, the urination information estimation system 100, according to one embodiment of the invention, may acquire a sound signal of a predetermined length or a plurality of sound signals from the device 200 before acquiring the sound signal related to the urination of the user, and compare and analyze the acquired sound signal(s) and a reference sound signal (e.g., a reference sound signal according to each of the positions, number, types, kinds, and characteristics of the sound acquisition modules) to specify information on the positions, number, types, kinds, characteristics, and the like of the sound acquisition modules included in the device 200, and correct a deviation occurring in the sound signal related to the urination of the user with reference to the specified information.

Next, the urination information estimation system 100, according to one embodiment of the invention, may calculate urination parameters related to an effective (RMS) value and a spectral centroid from the acquired sound signal.

Next, the urination information estimation system 100, according to one embodiment of the invention, may estimate a urine flow rate, urination start and end points, and a voided urine volume of the user with reference to the calculated urination parameters.

Meanwhile, according to one embodiment of the invention, a certain pattern of fine vibration may occur in the device 200 when the user is holding the device 200 while urinating, and such vibration may not occur when the device 200 is fixed or put in a certain place (i.e., when the user is not holding the device 200). Thus, the urination information estimation system 100, according to one embodiment of the invention, may acquire information on the user's motion occurring while urinating from the device 200 of the user, and estimate the urine flow rate with further reference to the acquired information.

For example, the urination information estimation system 100, according to one embodiment of the invention, may specify a location of the device 200 of the user (e.g., whether the user urinates with the device 200 being held or with the device 200 being put in a certain place) with reference to information on the user's motion while urinating, and estimate a urine flow rate of the user using a urine flow rate prediction model associated with the specified location of the device 200. Meanwhile, the urination information estimation system 100, according to one embodiment of the invention, may filter noises from the acquired sound signal with reference to the information on the user's motion while urinating.

Next, the urination information estimation system 100 according to one embodiment of the invention may provide the user with information on the estimated urine flow rate, urination start and end points, and voided urine volume of the user via the device 200.

The embodiments according to the invention as described above may be implemented in the form of program instructions that can be executed by various computer components and may be stored on a computer-readable recording medium. The computer-readable recording medium may include program instructions, data files, and data structures, separately or in combination. The program instructions stored on the computer-readable recording medium may be specially designed and configured for the present invention, or may also be known and available to those skilled in the computer software field. Examples of the computer-readable recording medium include the following: magnetic media, such as hard disks, floppy disks and magnetic tapes; optical media, such as compact disk-read only memory (CD-ROM) and digital versatile disks (DVDs); magneto-optical media, such as floptical disks; and hardware devices, such as read-only memory (ROM), random access memory (RAM), and flash memory, which are specially configured to store and execute program instructions. Examples of the program instructions include not only machine language codes created by a compiler, but also high-level language codes that can be executed by a computer using an interpreter. The above hardware devices may be changed to one or more software modules to perform the processes of the present invention, and vice versa.

Although the present invention has been described above in terms of specific items, such as detailed elements as well as the limited embodiments and the drawings, they are only provided to help more general understanding of the invention, and the present invention is not limited to the above embodiments. It will be appreciated by those skilled in the art to which the present invention pertains that various modifications and changes may be made from the above description.

Therefore, the spirit of the present invention shall not be limited to the above-described embodiments, and the entire scope of the appended claims and their equivalents will fall within the scope and spirit of the invention.

What is claimed is:

1. A method for calculating urination information, the method comprising
placing a mobile device in a predetermined location adjacent a toilet bowl, where the location is one of upon a body of a user or on a specified surface proximate the user's body and proximate the toilet bowl;
receiving data including a sound signal and a motion signal, recorded by a mobile device at least during urination of the user into the toilet bowl;
wherein an amount of sound signal that is received is based on a duration value preprogrammed into the mobile device;
wherein the mobile device of the user is a smartphone, the smartphone including a microphone and acceleration sensor;
determining a sex of the user based on a determined frequency of the sound signal;
selecting a urine flow rate prediction model corresponding to the determined sex;
generating first segmented signals out of the sound signal according to a time domain from the sound signal;
obtaining period information indicating whether each of the first segmented signals corresponds to the urination or not by using first parameters derived from the first segmented signals;
generating second segmented signals out of the sound signal according to the time domain from the sound signal;
filtering a noise of the second segmented signals on the basis of the period information, wherein filtered second segmented signals include values in frequency domain;
wherein the filtering also utilizes the acquired motion signal from the mobile device;
obtaining information of a urine flow rate, a urination start point, a urination end point, and a total voided urine volume by using second parameters derived from each of the filtered second segmented signals and the selected urine flow rate prediction model;

and displaying on a display of the smartphone the urine flow rate information, the urination start point information, the urination end point information, and the total voided urine volume information.

2. The method of claim 1, wherein each of the first parameters is an effective value derived from each of the first segmented signals, and wherein each of the second parameters is an effective value derived from each of the second segmented signals.

3. The method of claim 1, wherein a voided urine volume of the user is obtained based on the start point and the end point of the urination and the information of the urine flow rate.

4. The method of claim 3, wherein a voiding diary of the user is generated based on at least one of the information of urine flow rate, the start point and the end point of the urination, and the voided urine volume.

5. The method of claim 4, wherein an analysis comment on the urination of the user is generated with reference to the voiding diary.

6. A non-transitory computer-readable recording medium having stored thereon a computer program for executing the method of claim 1.

\* \* \* \* \*